United States Patent [19]

Dastur et al.

[11] 4,150,000
[45] Apr. 17, 1979

[54] ALLYL ETHERS IN PERFUMERY

[75] Inventors: Khurshid P. Dastur, Satigny; Joseph J. Becker, Geneva, both of Switzerland

[73] Assignee: Firmenich Sa, Geneva, Switzerland

[21] Appl. No.: 903,244

[22] Filed: May 5, 1978

[30] Foreign Application Priority Data

May 16, 1977 [CH] Switzerland .......................... 6054/77

[51] Int. Cl.$^2$ .......................... C11B 9/00; A61K 7/46
[52] U.S. Cl. .................. 252/522; 252/89 R; 252/108; 568/616
[58] Field of Search .................... 252/522; 260/615 R, 260/614

[56] References Cited

U.S. PATENT DOCUMENTS

| | | | |
|---|---|---|---|
| 2,397,514 | 4/1946 | Staff | 260/615 R |
| 2,861,109 | 11/1958 | Sturzenegger | 252/522 |
| 2,863,926 | 12/1958 | Carpenter et al. | 260/615 R |
| 3,201,456 | 8/1965 | Urry | 252/522 |
| 3,676,500 | 7/1972 | Mantell et al. | 252/522 |

OTHER PUBLICATIONS

Alfred Treibs, Ang. Chem. 60, pp. 289–344, (1948).
Lucile Liston et al., J. Amer. Chem. Soc. 60, p. 1264, (1938).

*Primary Examiner*—Veronica O'Keefe
*Attorney, Agent, or Firm*—Pennie & Edmonds

[57] ABSTRACT

Novel allyl ethers are found to be useful as odor modifying ingredients. The new compounds are particularly useful in the preparation of perfumes and perfume compositions as well as for the manufacture or perfumed articles such as soaps, detergents and household materials in general.

4 Claims, No Drawings

ALLYL ETHERS IN PERFUMERY

SUMMARY OF THE INVENTION

The present invention provides new allyl ethers of formula

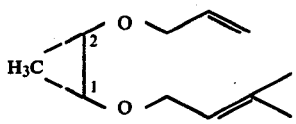

wherein the CH₃ radical is bound to the carbon atom of the main chain in position 1 or 2, also defined as 1-[3'-methyl-but-2'-en-1'-oxy]-2-[prop-2'-en-1'-oxy]-propane and 1-[prop-2'-en-1'-oxy]-2-[3'-methyl-but-2'-en-1'-oxy]-propane.

The invention relates also to a method for modifying, enhancing or improving the odour properties of perfumes, perfume bases and perfumed articles which method comprises the step of adding thereto a fragrance effective amount of one of the compounds of formula (I), or any mixture thereof.

The invention relates further to a perfume composition which comprises having added thereto a fragrance effective amount of one of the compounds of formula (I), or any mixture thereof.

Finally, the invention provides perfumed articles containing as perfume ingredient one of the compounds of formula (I), or any mixture thereof.

BACKGROUND OF THE INVENTION

In a continuous effort towards large scale production of chemicals having useful odorous properties, the perfume industry has constantly tried to convert odourless compounds which are cheaply available on the market into valuable fragrances.

By following this approach we have now unexpectedly found that propylene-glycol derivatives of formula (I) possess useful odorous properties and consequently can be advantageously used as perfume ingredients in the manufacture of perfumes, perfume bases and perfumed articles. Although compounds of analogous structure, namely derivatives of ethylene-glycol, have been prior described in the scientific literature, none of them presents odorous characters as pronounced and interesting as those possessed by the compounds of formula (I).

In J. Amer. Chem. Soc., 60, 1264 (1938) the compound of formula

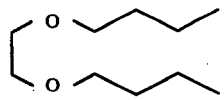

is namely described as being a compound presenting a musty odour reminiscent of mushroom, in much the same extent as the odour possessed by the analogous derivatives of formula

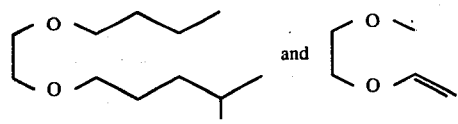

[see: Chem. Abstr. 1936, I 4711 and Canad. J. Res., 8, 208 (1933)]. The compound of formula

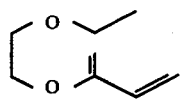

has been described as possessing a spicy smell [see: Angew. Chem., 60, 294 (1948)].

Hitherto, none of the above mentioned compounds has ever found a useful application in the perfumery field.

PREFERRED EMBODIMENTS OF THE INVENTION

The new compounds of the invention develop, in contradistinction with the prior known analogues, a natural fugacious scent of green, slightly flowery-aromatic character. Owing to its particular odorous qualities, the compounds of formula (I) can be used in a large variety of applications, namely for the manufacture of flowery compositions to which they confer a much appreciated naturalness.

Compounds (I) are particularly adapted to the perfuming of technical products, such as soaps, detergents, air fresheners as well as cosmetic materials, e.g. beauty creams, talcs, deodorizers and shampoos.

Typically, interesting effects in perfume compositions are achieved by using the compounds of formula (I) in proportions of from about 1 to about 20% by weight based on the total weight of the composition into which they are incorporated.

Concentrations smaller than the above given lower limits can be used in the perfuming of technical products, namely soaps and detergents.

The man in the art will appreciate that the concentration values can vary depending on the nature of the coingredients in a given composition and on that of the substrate to which they are added and that, consequently, said values cannot be interpreted restrictively.

Compounds (I), defined as 1-[3'-methyl-but-2'-en-1'-oxy]-2-[prop-2'-en-1'-oxy]-propane and 1-[prop-2'-en-1'-oxy]-2-[3'-methyl-but-2'-en-1'-oxy]-propane, are new chemical entities. They can be obtained starting from propylene-glycol by treating it with 2-methyl-but-3-en-2-ol in an acidic medium, followed by an addition of an allyl halide on the resulting secondary alcohol.

The process is illustrated in details hereinbelow.

a. A mixture of 200 g of propylene-glycol, 214 g of 2-methyl-but-3-en-2-ol and 20 g of acidic diatomaceous earth was kept under stirring during 20 h at about 90° C. After cooling and filtration, an extraction was effected with 1 l of diethyl ether, whereupon the combined organic extracts were washed, dried over anhydrous sodium sulphate and finally concentrated. The obtained residue was distilled to yield 114 g (yield 31.8%) of 3-[3'-methyl-but-2'-en-1'-oxy]-propan-2-ol and 2-[3'-methyl-but-2'-en-1'-oxy]-propan-1-ol; b.p. 77°–83° C./12 Torr.

NMR(CCl₄) : 1.07 (3H, d, J=6cps); 1.65 (3H, s); 1.75 (3H, s); 2.6 (1H, 1s); 5.25 (1H, m) δ ppm.

b. A solution of the alcohol obtained as indicated above (70 g) in 500 ml of anhydrous tetrahydrofuranne was added dropwise while stirring in 20 minute time to a suspension of 12 g of sodium hydride in 500 ml of anhydrous tetrahydrofuranne. The reaction mixture was kept under stirring at room temperature for 1½ h, then 60 g of allyl bromide in 120 ml of tetrahydrofuranne were added thereto and stirring was carried on for 16 supplementary hours while the mixture was heated to 70° C. After cooling, the excess of sodium hydride was decomposed with 5 ml of methanol and the mixture was evaporated to dryness. The obtained residue was extracted with 250 ml of diethyl ether and the organic extracts were washed with 200 ml of water. After drying over Na₂SO₄, evaporation and distillation, 54 g of the desired products (yield 60.3%) were collected at b.p. 40°–48° C./0.2 Torr.

NMR(CCl₄) : 1.1 (3H, d, J=6cps); 1.65 (3H, s); 1.75 (3H, s); 4.9–6.2 (4H, m) δ ppm;

IR(film) : 1690, 1660, 1470, 1390, 1100 and 940 cm⁻¹.

The product, such as obtained by the process described above, is perfectly adapted to all of the practical and industrial applications considered in the present invention. It is clear however that the first step of the above given process enables the preparation of an alcohol whose structure is better defined as follows

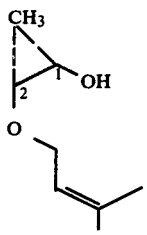

i.e. the methyl radical can be bound to the carbon atom of position 1 or 2 and, consequently, the allyl ether obtained therefrom (see step b.) occurs in the form of a mixture of positional isomers.

The constituents of this mixture can be separated one from the other by means of conventional techniques, such as preparative vapour phase chromatography. The isolated compounds showed the following analytical characters.

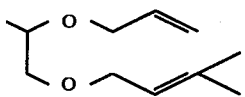
(Ia)

NMR(CDCl₃) : 1.15 (3H, d, J=6cps); 1.65 (3H, s); 1.75 (3H, s); 3.2–4.2 (7H, m); 5.0–6.3 (4H, m) δ ppm;

$t_R$=4.56 mn (5% CARBOWAX® 20M, 130° C., 3m).

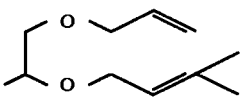
(Ib)

NMR(CDCl₃) : 1.15 (3H, d, J=6cps); 1.65 (3H, s); 1.75 (3H, s); 3.2–4.2 (7H, m); 5.0–6.3 (4H, m) δ ppm;

R=4.68 mn (5% CARBOWAX® 20M, 130° C., 3m).

We have observed that the separation of isomers was made easier whenever it was performed on the isomeric mixture of the alcohols obtained in the first step (see step a.) of the process. Thus, by using a CARBOWAX® 20M column (120° C., 5%, 3m) it was possible to separate each isomer by vapour phase chromatography. Hereinbelow are reproduced their respective analytical characters.

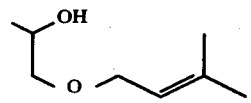
(IIa)

NMR(CCl₄) : 1.05 (3H, d, J=6cps); 1.65 (3H, s); 1.75 (3H, s); 2.6 (1H, s); 2.9–3.4 (2H, m); 3.5–3.8 (1H, m); 3.9 (3.9 H, d, J=8cps); 5.05–5.4 (1H, m) δ ppm;

IR(film) : 3400, 2900, 1680, 1390, 1100 cm⁻¹;

$t_R$(=retention time): 6.72 mn.

Its isomer of formula

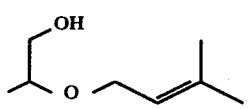
(IIb)

was present in a 30% concentration in the mixture and showed the following analytical data.

NMR(CCl₄) : 1.07 (3H, d, J=6cps); 1.67 (3H, s); 1.75 (3H, s); 2.65 (1H, s); 3.4 (3H, m); 3.95 (2H, d, J=8cps); 5.1–5.45 (1H, m) δ ppm;

IR(film) : 3400, 2900, 1680, 1390, 1100 cm⁻¹;

$t_R$=8.88 mn.

EXAMPLE

A base perfume composition of flowery type was prepared by admixing the following ingredients (parts by weight):

| | |
|---|---|
| Phenethylol | 150 |
| Terpineol | 100 |
| ter-Butylcyclohexyl acetate | 100 |
| Cinnamic alcohol | 80 |
| Hydratropic alcohol | 60 |
| Rose-wood oil of Brazil | 60 |
| Cyclohexylethyl acetate | 60 |
| 2,4-Dimethyl-cyclohex-3-en-1-yl carbaldehyde 10%* | 60 |
| Benzyl salicylate | 60 |
| Synthetic lily-of-the-valley oil | 50 |
| Cyclamen aldehyde | 20 |
| Hexyl salicylate | 20 |
| Isobutyl benzoate | 20 |
| Galbanum oil 10%* | 20 |
| Iso-nonyl aldehyde 10%* | 20 |
| Isopropylcyclohexylmethanol[1] | 10 |
| Methyl nonyl aldehyde 10%* | 10 |
| | 900 |

*in diethyl phthalate
[1]MAYOL®, Firmenich SA, see Swiss patent No. 578,312

By adding to 90 g of the above base 10 g of the product obtained according to the process described sub letters a. and b. above, there was obtained a novel composition whose odorous characters were more natural and aromatic than those of the base composition. The novel composition possessed moreover an enhanced top note.

What we claim is:
1. 1-[3'-Methyl-but-2'-en-1'-oxy]-2-[prop-2'-en-1'-oxy]-propane.
2. 1-[Prop-2'-en-1'-oxy]-2-[3'-methyl-but-2'-en-1'-oxy]-propane.
3. Method for modifying, enhancing or improving the odour properties of perfumes, and perfume bases which comprises the step of adding thereto a fragrance effective amount of one of the compounds of claim 1 or 2, or any mixture thereof.
4. A perfume composition which comprises having added thereto a fragrance effective amount of one of the compounds of claim 1 or 2, or any mixture thereof.

* * * * *